(12) United States Patent
Kajino et al.

(10) Patent No.: US 8,361,662 B2
(45) Date of Patent: Jan. 29, 2013

(54) ELECTROCATALYST AND ENZYMATIC ELECTRODE

(75) Inventors: Tsutomu Kajino, Toyoake (JP);
Norihiko Setoyama, Aichi-ken (JP);
Keiko Uemura, Seto (JP); Hisao Kato, Brussels (BE); Kenji Kano, Kyoto (JP);
Seiya Tsujimura, Kashihira (JP);
Takeshi Sakurai, Kanazawa (JP);
Kunishige Kataoka, Kanazawa (JP)

(73) Assignees: Toyota Jidosha Kabushiki Kaisha, Toyota-shi, Aichi-ken (JP); Kyoto University, Kyoto-fu (JP); National University Corporation Kanazawa University, Ishikawa-ken (JP)

( * ) Notice: Subject to any disclaimer, the term of this patent is extended or adjusted under 35 U.S.C. 154(b) by 771 days.

(21) Appl. No.: 12/440,089

(22) PCT Filed: Sep. 5, 2007

(86) PCT No.: PCT/JP2007/067304
§ 371 (c)(1),
(2), (4) Date: Oct. 20, 2009

(87) PCT Pub. No.: WO2008/029843
PCT Pub. Date: Mar. 13, 2008

(65) Prior Publication Data
US 2010/0040910 A1    Feb. 18, 2010

(30) Foreign Application Priority Data
Sep. 5, 2006   (JP) ................. 2006-240867

(51) Int. Cl.
*H01M 8/16*   (2006.01)
*H01L 31/00*  (2006.01)
*C12Q 1/00*   (2006.01)

(52) U.S. Cl. .............. 429/401; 136/263; 204/403.14
(58) Field of Classification Search ............... 429/401; 136/263; 204/403.14
See application file for complete search history.

(56) References Cited

U.S. PATENT DOCUMENTS
2007/0196659 A1 * 8/2007 Setoyama et al. ........... 428/408

FOREIGN PATENT DOCUMENTS
| JP | 2004-300328 | | 10/2004 |
| JP | 2005-343775 | | 12/2005 |
| JP | 2006-58289 | | 3/2006 |
| JP | 2006-096653 | * | 4/2006 |
| WO | WO 2005/122315 A1 | | 12/2005 |

OTHER PUBLICATIONS

JP 2004-300328 to Higiwara (machine translation).*

(Continued)

*Primary Examiner* — Patrick Ryan
*Assistant Examiner* — Alex Usyatinsky
(74) *Attorney, Agent, or Firm* — Finnegan, Henderson, Farabow, Garrett & Dunner, LLP

(57) ABSTRACT

A novel electrocatalyst made of an oxidase having high electron transfer efficiency and an enzymatic electrode using the same are provided. The electrocatalyst is made of CueO. The enzymatic electrode comprises a carbonaceous porous body and an electrocatalyst made of CueO supported on the surface of the carbonaceous porous body. CueO is preferably CueO from *Escherichia coli*. The carbonaceous porous body constituting the enzymatic electrode is preferably carbonaceous gel. Also, the enzymatic electrode may further comprise a mediator which facilitates transfer of electron between the carbonaceous porous body and said CueO.

8 Claims, 3 Drawing Sheets

OTHER PUBLICATIONS

Roberts, S. et al, "Crystal Structure and Electron Transfer Kinetics of CueO, a Multicopper Oxidase Required for Copper Homeostasis in *Escherichia coli*"; PNAS, Mar. 5, 2002, vol. 99, No. 5, pp. 2766-2771.

Kataoka, K., Structure and Function of Multicopper Oxidoreductases, Biochemistry, 2005, vol. 77, pp. 148-153.

Y. Kamitaka et al., Abstract of "Bioelectrocatalysis of Dioxygen Reduction with Multi-Copper Oxidases," Lecture Summary of Meeting of The Electrochemical Society of Japan, vol. 73, p. 211 (1J09) (2006).

Extended European Search Report dated Dec. 30, 2009 for EP Appl. No. 07806747.7.

Shleev, S. et al., "Direct electron transfer between copper-containing proteins and electrodes," Biosensors & Bioelectronics, vol. 20, (2005), pp. 2517-2554.

Miura, Y. et al., Bioelectric Reduction of $O_2$ Catalyzed by CueO from *Escherichia coli* Adsorbed on a Highly Oriented Pyrolytic Graphite Electrode, Chemistry Letters, vol. 36, No. 1, (2007), pp. 132-133.

* cited by examiner

ELECTROCATALYST AND ENZYMATIC ELECTRODE

CROSS-REFERENCE TO RELATED APPLICATIONS

This application is a national phase application of International Application No. PCT/JP2007/067304, filed Sep. 5, 2007, and claims the priority of Japanese Application No. 2006-240867, filed Sep. 5, 2006, the contents of both of which are incorporated herein by reference.

TECHNICAL FIELD

The present invention relates to an electrocatalyst and an enzymatic electrode, particularly, enzymatic electrodes used for electrochemical devices such as biosensors and fuel cells, and electrocatalysts used for enzymatic electrodes.

BACKGROUND ART

Enzymes are biocatalysts which drive chemical reactions (metabolism) in vivo. Enzymes are primarily constructed by protein. There are enzymes which consist of protein alone, but most of the enzymes require components (cofactors) other than protein to express catalytic activity or enhance catalytic activity.

Enzymes have the following features:

(1) enzymes perform catalytic reactions under moderate conditions such as ordinary temperature and ordinary pressure; and (2) enzymes have both "substrate specificity" to react only with a specific substrate (a substance subjected to the action of the enzyme), and "reaction specificity" to catalyze a specific chemical reaction without side reactions.

Enzymes which catalyze oxidoreduction in vivo are called as "oxidoreductases". Among the enzymes, oxidoreductases which oxidize substrates using oxygen as an electron acceptor are particularly called as "oxidases", and which reduce substrates are particularly called "reductases". When a certain oxidoreductase is immobilized on the surface of an electrode, only a specific redox reaction selectively proceeds on the electrode surface by the catalytic action of the enzyme, and the change in the substance concerned in the redox reaction can be converted to an electrical signal by the electrode. Such an electrode is called "enzymatic electrode" and has been utilized as the electrode for various biosensors, fuel cells and so on.

In order to use an enzyme as an electrocatalyst, the enzyme needs to be immobilized on the surface of an appropriate carrier. However, since enzymes are soluble in water in general, there occurs a problem that the enzyme easily dissolves during use.

In addition, each enzyme has a part (active center) to which a substrate is specifically bound and where the catalytic reaction proceeds. Since the active center is often located deep in a complex three-dimensional structure of the protein molecule, it is difficult to perform a direct transfer of electron between the active center and the electrode. In this case, a low-molecular substance which gets into the active site of the enzyme, transfers electron with enzyme, and carries electron to the electrode is generally used together. Such a low-molecular substance is called "mediator". However, since the electron transfer rate between enzyme and mediator depends on their molecular motion, the electron transfer rate is not necessarily rapid enough, limiting the current density of the enzymatic electrode.

In order to solve this problem, various ideas have been proposed.

For example, Patent Literature 1 discloses a nitrogen-containing carbonaceous composite material comprising a porous body made of a nitrogen-containing carbonaceous material having skeleton structure formed by carbon atoms and nitrogen atoms, and an oxidoreductase supported by the porous body.

The following is mentioned in Patent Literature 1:

(1) association between protein and carrier can be strengthened in such a manner that new bonds such as hydrogen bonds are generated between polar portions of the nitrogen-containing carbonaceous material and hydrophilic groups on the surface of the protein when the oxidoreductase is supported by the nitrogen-containing carbonaceous material, because the polar portions are scattered on the porous surface of the nitrogen-containing carbonaceous material; and (2) examples of the oxidoreductase to be supported on a carrier are laccase, diaphorase, lipoxyamide dehydrogenase, alcohol dehydrogenase, glucose oxidase and oxidases which use sugars other than glucose as substrate, and glucose dehydrogenase and dehydrogenases which use sugars other than glucose as substrate.

Also, Patent Literature 2 discloses an enzymatic electrode comprising a conductive member, an enzyme, a first mediator and a second mediator, wherein the first mediator and the second mediator with different oxidoreduction potentials are immobilized on the conductive member by a carrier.

The following is mentioned in Patent Literature 2:

(1) density of the supported enzyme per effective surface area of the conductive member can be raised by the constitution above being employed;

(2) a second mediator, which transfers charge between the first mediator and the conductive member, is used in addition to the first mediator, which can quickly transfer electron with the enzyme, so that the enzymatic electrode can quickly transfer electron with the enzyme; and (3) examples of the enzyme are glucose oxidase, galactose oxidase, bilirubin oxidase, pyruvate oxidase, D-amino-acid oxidase, L-amino-acid oxidase, amine oxidase, cholesterol oxidase, ascorbic acid oxidase, cytochrome oxidase, alcohol dehydrogenase, glutamate dehydrogenase, cholesterol dehydrogenase, aldehyde dehydrogenase, glucose dehydrogenase, fructose dehydrogenase, sorbitol dehydrogenase, lactate dehydrogenase, malic dehydrogenase, glycerol dehydrogenase, 17B hydroxysteroid dehydrogenase, estradiol 17B dehydrogenase, amino-acid dehydrogenase, glyceraldehydes 3-phosphate dehydrogenase, 3-hydroxysteroid dehydrogenase, diaphorase, catalase, peroxidase, glutathione reductase, NADH-cytochrome b5 reductase, NADPH-adrenoxin reductase, cytochrome b5 reductase, adrenodoxin reductase, and nitrate reductase.

CITATION LIST

Patent Literature

Patent Literature 1: Japanese Patent Application Laid-Open (JP-A) No. 2005-343775.
Patent Literature 2: JP-A No. 2006-058289.

SUMMARY OF INVENTION

Technical Problem

Oxidoreductase generally has an active center which binds a substrate and a site (electron transfer gate) which transfers electron to/from the active center. Since electron transfer to/from enzyme in vivo is generally mediated by a mediator, the electron transfer gate of enzyme is often buried inside of the pocket of protein molecule. When the enzyme in such a state is immobilized on the surface of an electrode, it is unavoidable that the distance between the electron transfer gate and the surface of the electrode becomes long. Since common logarithm of the electron transfer rate slows down in proportion to distance, enzymes hitherto known cannot provide a high efficiency in the electron transfer.

In order to solve this problem, using a mediator may be effective as disclosed in Patent Literature 2. However, there is a limit to improve the efficiency of electron transfer when merely using a mediator. In addition, no enzyme suitable for enzymatic electrode capable of obtaining sufficient current density has been reported.

An object of the present invention is to provide a novel electrocatalyst made of an oxidase having high electron transfer efficiency, and an enzymatic electrode using the same.

Solution to Problem

In order to attain the above object, an electrocatalyst of the present invention is made of CueO.

Also, an enzymatic electrode of the present invention comprises a carbonaceous porous body and an electrocatalyst made of CueO supported on the surface of the carbonaceous porous body.

Advantageous Effects of Invention

When CueO, a member of multi-copper oxidases, is used as a catalyst for the enzymatic electrode, a higher current density can be obtained compared with conventional oxidoreductases.

The reasons for this are considered to be as follows:

(1) since the active center, which catalyzes the oxidation reaction, and the electron transfer gate are separated in the enzyme molecule of CueO, the catalytic reaction and the electron transfer can be independently achieved even if the enzyme is immobilized on a solid surface of electrode; and (2) since the electron transfer gate of CueO is located closer to molecular surface than that of other enzymes, the distance between the electron transfer gate and the electrode decreases when the CueO is immobilized on the solid surface so that the efficiency of electron transfer improves.

As aforementioned, the electrocatalyst of the present invention is excellent in electron transfer efficiency, and can obtain higher current density compared to the cases other oxidoreductases are used. That is, the enzymatic electrode having the electrocatalyst of the present invention immobilized in a limited area is able to produce high current values per immobilization amount of electrocatalyst. Specifically, current density equivalent to that of the electrode using platinum catalyst can be obtained by using the present enzymatic electrode. Moreover, the enzymatic electrode having the electrocatalyst of the present invention immobilized can produce high current values even at a small amount of immobilized electrocatalyst. Thus, cost reduction is possible.

Further, the electrocatalyst of the present invention realizes a high electron transfer efficiency. That is, since the electron transfer rate between electrode and electrocatalyst is very fast, high current value can be obtained even without using a mediator for an improvement of the electrode reaction rate by the enzymatic electrode.

Also, since the electrocatalyst of the present invention shows high electron transfer efficiency, and the electron transfer rate between the electrode and the electrocatalyst is very rapid, catalyst current obtained by using the enzymatic electrode having the electrocatalyst of the present invention immobilized reaches diffusion limit of the oxygen supply rate to electrode in contrast to the enzyme activity shown by the electrocatalyst. That is, the enzymatic electrode having the electrocatalyst of the present invention immobilized shows stable electrode activities and can produce stable output. Therefore, by using the enzymatic electrode having the electrocatalyst of the present invention immobilized, output of fuel cell can be improved and the sensitivity of oxygen detecting-type sensor can be increased.

DESCRIPTION OF EMBODIMENTS

Figure 1:
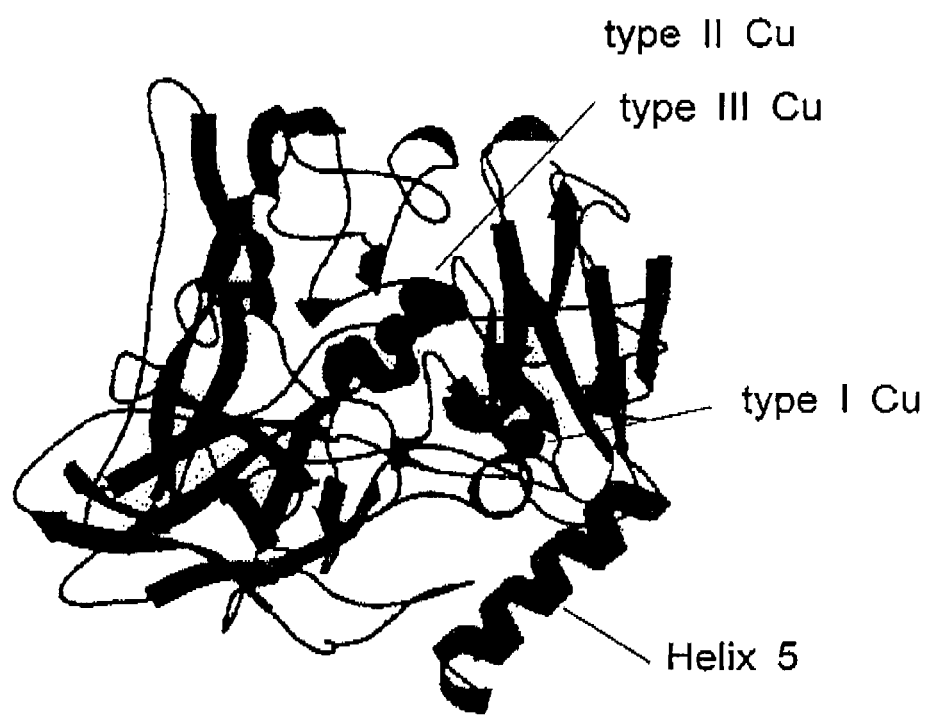
FIG. 1 shows a molecular structure of CueO from *Escherichia coli*, which is a kind of multi-copper oxidases.

Hereinafter, the embodiment of the present invention will be explained in more detail.

An electrocatalyst according to the present invention is made of CueO.

Oxidoreductase is the enzyme which catalyzes a redox reaction and has an active center and an electron transfer gate in a three-dimensional structure of the protein molecule. The "active center" refers to a part to which a substrate is specifically bound and allows a catalytic reaction. The "electron transfer gate" refers to a part which transfers electron to/from the active center.

Oxidoreductase can be classified into oxidase which oxidizes a substrate, and reductase which reduces a substrate. Depending on polarity of electrode, either enzyme is used as electrocatalyst. That is, in the case that an enzyme is used as the material on the positive electrode side, the oxidase, which can receive electron or can catalyze the reaction to produce water using proton and oxygen as substrates, is used. On the other hand, in the case that an enzyme is used as the material on the negative electrode side, a reductase, which releases electron in the reaction, is used.

Also, the oxidoreductase is a macromolecule having a specific three-dimensional structure, and its active center and electron transfer gate are generally located deep in an opening (pocket or cranny) of a three-dimensional structure of the protein molecule. In this case, the gates of the active center and the electron transfer may be in the same or different opening.

Among various oxidoreductases, the oxidoreductases having a first opening constituting the electron transfer gate and a second opening constituting an active center, are able to perform very smooth transfer of substrate when the enzyme catalyzes the substrate. Thus, the electron transfer efficiency between enzyme and electrode of oxidoreductases above improves compared to that of enzymes containing the active center and electron transfer gate in the same opening.

Particularly, oxidoreductase having the electron transfer gate at the first opening on the opposite side of the second opening constituting the active center is able to perform the electron transfer between electrode and electron transfer gate quite smoothly by locating the first opening close to the surface of the electrode. Thus, the electron transfer efficiency between enzyme and electrode further improves.

Herein, "the first opening on the opposite side of the second opening" means the angle between the normal direction of a surface with the first opening and the normal direction of a surface with the second opening is larger than 90°. The angle between two normals is preferably large, more preferably close to 180°.

Among various oxidoreductases, multi-copper oxidase catalyzes the reaction to reduce molecular oxygen to water in the four-electron process with the use of electrons extracted from substrate. Multi-copper oxidase has a mononuclear blue copper (type I Cu) functioning as the electron transfer gate and a trinuclear copper cluster (type II Cu, type III Cu) being an active center. The mononuclear blue copper and the trinuclear copper cluster are located inside of different openings. Further, one of two openings is located on the front face of the three-dimensional structure of the protein molecule, and the other on the rear face thereof. Thus, multi-copper oxidase or modified enzymes, which are multi-copper oxidases modified by genetic engineering, are particularly suitable as a catalyst for the enzymatic positive electrode used for various electrochemical devices such as biosensors and fuel cells.

Examples of the multi-copper oxidases are, specifically, laccase, bilirubin oxidase, ascorbic acid oxidase, ceruloplasmin, CueO and endospore coat protein CotA of *Bacillus* bacteria. Among them, CueO, particularly, copper metabolism-related oxidase CueO of *Escherichia coli* (CueO from *Escherichia coli* (*Escherichia coli*-derived CueO)) can produce higher current density than conventional oxidoreductases when it is used as electrocatalyst for enzymatic electrode.

"CueO" means a kind of multi-copper oxidases collected from various strains. Also, "CueO from *Escherichia coli*" means CueO extracted from *Escherichia coli*. The amino-acid sequence of a wild type mature CueO (Swiss-Prot accession: Q8X947) is shown in Sequence ID No. 1 of Sequence Listing.

CueO may be the wild type CueO directly extracted from a strain or modified CueO, of which a part of amino-acid sequence is changed or deleted by genetic engineering, as far as catalytic activity and electron transfer ability are retained.

Next, an enzymatic electrode of the present invention will be explained.

An enzymatic electrode of the present invention comprises a carbonaceous porous body and an electrocatalyst made of CueO supported on the surface of the carbonaceous porous body. Particularly, CueO is preferably that obtained from *Escherichia coli*. Among the components, explanations of CueO and CueO from *Escherichia coli* are as mentioned above.

As a carrier supporting the enzyme, a carbonaceous porous body is used. The carbonaceous porous body is particularly suitable for the carrier since the carbonaceous porous body not only can perform a smooth electron transfer between enzyme and electrode, but also can physically support the enzyme in the pore appropriate in size, and can even restrain the enzyme from deactivation.

In order to sufficiently improve stability and activity of the enzyme, which is a supported component, it is preferable that the carbonaceous porous body satisfies one or more conditions [1.] to [4.] mentioned below.

[1. Averaged Pore Size]

It is preferable that the carbonaceous porous body has an averaged pore size of 2 to 50 nm, more preferably 2 to 20 nm. If the averaged pore size is less than 2 nm, the pore size of the carbonaceous porous body is often smaller than that of the enzyme, thus, its adsorption property decreases. On the other hand, if the averaged pore size exceeds 50 nm, the specific surface area lowers, and adsorption property decreases. Also, if the averaged pore size exceeds 20 nm, problems may be likely to occur upon supporting some enzymes.

Also, it is preferable that the averaged pore size of carbonaceous porous body is larger than the molecular size of enzyme, more preferably 1 to 1.25 times larger than the molecular size of enzyme. If the averaged pore size of carbonaceous porous body is within the above range, the enzyme is easily immobilized within the pore. When the enzyme is immobilized within the pore, the outer wall of the pore prevents a change in the structure of the enzyme by heat. Thus, deactivation of enzyme by heat can be prevented so as to improve thermal stability.

The averaged pore size means the pore size value of distribution peak top in a pore size distribution obtained by a nitrogen adsorption isotherm described hereinafter.

[2. Pore Size Distribution]

It is preferable that a pore volume of the carbonaceous porous body in ±25% of the averaged pore size accounts for 60% or more of total pore volume in the pore size distribution range from 2 to 100 nm. If uniformity of pore size is worse than the above distribution, the amount of pore not having the size suitable for supporting enzyme increases so that the stability and activity of enzyme may be insufficient.

[3. Specific Surface Area]

It is preferable that the carbonaceous porous body has a specific surface area of 100 $m^2/g$ or more, more preferably 500 to 1000 $m^2/g$. If the specific surface area of carbonaceous porous body is less than 100 $m^2/g$, a contact area of carbonaceous porous body with the enzyme decreases, and pores adsorbing enzyme decrease so that adsorption property of enzyme decreases.

[4. Pore Volume]

A pore volume of the carbonaceous porous body may not be particularly limited as it varies due to the specific surface area and the averaged pore size, but is preferably 0.1 to 50 ml/g, more preferably 0.2 to 2.5 ml/g.

Also, the total volume of the pore having the size larger than the molecular size of enzyme among pores of the carbonaceous porous body is preferably larger than total volume of supported enzyme.

The specific surface area and the pore volume of the carbonaceous porous body can be measured by the following general volumetric method.

Specifically, the carbonaceous porous body is charged in a container to cool to liquid nitrogen temperature (−198° C.). Nitrogen gas is introduced in the container. The adsorbed amount of nitrogen gas is obtained by the volumetric method. Next, the pressure of nitrogen gas introduced is gradually increased. The adsorbed amount of nitrogen gas with respect to equilibrium pressure is plotted to obtain the nitrogen adsorption-desorption isotherm. With the use of the nitrogen adsorption-desorption isotherm, the specific surface area and the pore volume can be calculated by SPE (Subtracting Pore Effect) method (K. Kaneko, C. Ishii, M. Ruike, H. Kuwabara, Carbon 30, 1075, 1986). The SPE method is a method to calculate specific surface area or the like by performing micropore analysis with the use of the αs-plot method, the t-plot method or the like and removing the effect of strong potential field of micropore. The SPE method has higher accuracy than the BET method in calculating the specific surface area of microporous porous body or the like.

Also, the pore size distribution and the pore size value of distribution peak top can be obtained by the BJH analysis of the nitrogen adsorption-desorption isotherm (Barret E. P., Joyner L. G., Halenda P. H., Journal of American Chemical Society 73, 373, 1951).

Specifically, examples of the carbonaceous porous body satisfying the above condition are the following [1.] to [3.].

[1. Mesoporous Carbonaceous Particle]

A first specific example of the carbonaceous porous body is a mesoporous carbonaceous particle. The "mesoporous carbonaceous particle" is a porous carbonaceous material in which meso size (2 to 10 nm) pores are regularly disposed, wherein a ratio of a total pore volume in the pore size distribution range from 2 to 10 nm (total pore volume "S") to a total pore volume in the pore size distribution range from 2 to 100 nm (total pore volume "$S_0$"), which can be represented as "$S \times 100/S_0$", is 80% or more. The pore size distribution can be measured by the XRD method or the nitrogen adsorption method.

[2. Carbonaceous Gel]

A second specific example of the carbonaceous porous body is carbonaceous gel. The "carbonaceous gel" is a porous carbonaceous material in which meso size pores are irregularly disposed, and satisfies the following conditions (I) and (II):

(I) there is no X-ray diffraction peak in the scan region $2\theta=0.5°$ to $10°$ (CuK$\alpha$); and (II) in a pore size distribution calculated from an adsorption-desorption isotherm, in the case that a pore size of distribution peak top is in the range from 2 nm or more to less than 10 nm (pore size "d"), 60% or more of total pore volume is in the pore size range of d±2 nm, and in the case that the pore size of the distribution peak top is in the range from 10 nm or more to 50 nm or less (pore size "D"), 60% or more of total pore volume is in the pore size range of from (0.75×D) nm to (1.25×D) nm.

The condition (I) represents absence of the meso size pore regularly disposed. The X-ray diffraction peak shows that a periodic structure of the "d" value corresponding to the peak angle is present in a sample. Thus, a carbonaceous porous body having one or more peaks in the scan region $2\theta=0.5°$ to $10°$ (CuK$\alpha$) has pores regularly disposed with a period of 0.9 nm to 17.7 nm, and is a so-called mesoporous carbon (MPC).

On the other hand, the carbonaceous gel does not have an X-ray diffraction peak in the scan region, $2\theta=0.5°$ to $10°$ (CuK$\alpha$). It means that pores in the carbonaceous gel are not periodically disposed. The carbonaceous gel has a three-dimensional network structure, wherein pores are mutually connected. When the carbonaceous gel is used as a carrier, the stability and activity of enzyme improves compared to using the mesoporous carbon due to unknown reason in detail.

In the X-ray diffraction measurement (XRD), the peak in which a ratio of peak intensity to background noise intensity is less than 3 is not recognized as an X-ray diffraction peak. Thus, "there is no X-ray diffraction peak in scan region $2\theta=0.5°$ to $10°$ (CuK$\alpha$)" means that no X-ray diffraction peak in which a ratio of peak intensity to background noise intensity is more than 3 is observed in the scan region, $2\theta=0.5°$ to $10°$ (CuK$\alpha$).

The condition (II) represents uniformity of pore size. If the pore distribution is within the above range, the amount of pore having pore size suitable for supporting enzyme increases so that the stability and activity of enzyme improves.

The carbonaceous gel preferably satisfies the following condition (III) besides the above conditions (I) and (II):

(III) the pore size of distribution peak top in the pore size distribution of the carbonaceous gel is 2 to 20 nm.

If the pore size of the carbonaceous gel is less than 2 nm, the pore size of the carbonaceous porous body is often smaller than that of the enzyme, thus adsorption property decreases. On the other hand, if the pore size exceeds 50 nm, the specific surface area lowers, thus adsorption property decreases. Also, if the pore size of the distribution peak top exceeds 20 nm, problems may be likely to occur upon supporting the enzyme.

[3. Nitrogen-Containing Carbonaceous Gel]

The third example of carbonaceous porous body is a nitrogen-containing carbonaceous gel. The "nitrogen-containing carbonaceous gel" means a carbonaceous gel, at least a vicinity of surface of which is nitrogen-containing carbon. The "surface" includes not only an outer surface of the porous body but also an inner surface of the porous body. The carbonaceous gel, of which a vicinity of surface is constructed by nitrogen-containing carbon has an advantage of improvements in the supported amount, stability and activity of enzyme.

The atomic ratio of nitrogen and carbon (N/C ratio) in the nitrogen-containing carbonaceous gel is preferably 0.01 or more. If the N/C ratio is less than 0.01, the nitrogen atom decreases so that the adsorption site capable to interact with the enzyme decreases. The N/C ratio is more preferably 0.05 or more.

On the other hand, the N/C ratio is preferably 0.4 or less. If the N/C ratio exceeds 0.4, the strength of carbon skeleton declines so that the pore structure may be difficult to be maintained. The N/C ratio is more preferably 0.3 or less.

The N/C ratio of the nitrogen-containing carbon can be obtained by CHN elemental analysis or XPS. For further explanation of the nitrogen-containing carbonaceous gel besides the above, refer to the explanation of the carbonaceous gel.

The enzyme, which is an electrocatalyst, is supported on the surface of a carrier. The "surface of carrier" means the outer surface of the carrier and the inner surface of the pore. At least a part of enzyme is preferably supported on the inner surface of pore. The amount of enzyme supported in the pore is not limited, but the more is the better.

The amount of enzyme supported by carrier is not particularly limited if the enzyme activity is exhibited. Generally, if the supported amount of enzyme increases, a higher activity is obtained. In order to obtain sufficient activity from a practical viewpoint, the supported amount of enzyme is preferably 0.01 parts by mass or more based on 100 parts by mass of carbonaceous porous body. On the other hand, if an excess amount of enzyme is supported, the effect is saturated and unprofitable. Thus, the supported amount of enzyme is preferably 80 parts by mass or less based on 100 parts by mass of carbonaceous porous body.

The enzymatic electrode of the present invention may comprise the above-mentioned carrier and enzyme alone, or a mediator which facilitates transfer of electron between the carbonaceous porous body and the enzyme may also be supported on the carrier. In the enzymatic electrode of the present invention, the electron transfer efficiency of an enzyme being electrocatalyst is quite high so that a rate-determining step is the oxygen supply rate rather than electron transfer reaction between electrode and enzyme. Hence, the enzymatic electrode of the present invention can obtain a high current value without mediator, but the present invention does not exclude an use of mediator, and a mediator may be used, if necessary.

Examples of the mediator are, specifically, ABTS, metallocyanide such as WCN, and an Os complex. The mediator is desirably immobilized on the surface of the electrode. Thus, the mediator is desirably bound to a polymer such as poly-1-vinyl imidazole and insolubilized. Also, the mediator may be directly immobilized on the carbon carrier. The mediator may be used alone or in combination of two or more kinds.

In the enzymatic electrode of the present invention, if a carrier is in a sheet form, the carrier, which is electron-conductive and the surface of which supports enzyme (if necessary, mediator), can be used as an electrode. On the other hand, it the carrier is in a powder form, the carrier supporting enzyme may be immobilized on the surface of an appropriate metal electrode (for example, Pt electrode) for use.

Next, a method of producing the carbonaceous porous body used as the carrier will be explained. Among carbonaceous porous bodies, the mesoporous carbon, the carbonaceous gel and the nitrogen-containing carbonaceous gel may be produced by the following methods.

[1. Method of Producing Mesoporous Carbon]

A method to produce the mesoporous carbonaceous particle may not be particularly limited. For example, the mesoporous carbonaceous particle may be produced by the following method. A porous particle (mold) of silica, titania or the like having meso size pores regularly disposed is impregnated with or adsorbs an organic molecule such as sucrose, furfuryl alcohol or the like, followed by carbonization in an inert atmosphere. Next, the mold is dissolved by fluorinated acid, NaOH/EtOH or the like and removed, thus obtained mesoporous carbonaceous particles. As mold, for example, silica mesoporous body MCM-48 may be used.

[2. Method of Producing Carbonaceous Gel]

A method to produce the carbonaceous gel may not be particularly limited. For example, the carbonaceous gel can be produced by the following method.

In the first step, an organic gel is synthesized based on a method disclosed in the reference (R. W. Pekala, C. T. Alviso, F. M. Kong, and S. S. Hulsey, J. Non-cryst. Solids, vol. 145, (1992), pp. 90).

Specifically, a phenol resin such as resorcinol is reacted with aldehyde such as formaldehyde in the presence of alkali catalyst or acid catalyst, and is aged to obtain an organic gel made of phenol resin. Next, the obtained organic gel is dried, and fired in an inert atmosphere to carbonize, thus, a carbonaceous gel is obtained.

[3. Method of Producing Nitrogen-Containing Carbonaceous Gel]

A method of producing a nitrogen-containing carbonaceous gel is not particularly limited. For example, the nitrogen-containing carbonaceous gel may be produced by the following method.

(A) Method of Introducing Nitrogen Atom to Carbonaceous Gel Using Nitric Monoxide.

A nitrogen atom can be introduced into a carbonaceous gel, for example, based on a method disclosed in the reference (P. Chambrion et al., Energy & Fuels vol. 11, p. 681-685 (1997)). Specifically, a carbonaceous gel is set in a quartz reaction tube followed by heating to about 950° C. under helium stream. Next, NO (concentration: about 1,000 ppm) diluted by helium is introduced into the reaction tube to react at the reaction temperature of about 600 to 900° C. The reaction time for the reaction is not particularly limited. If the reaction time extends, the amount of nitrogen taken to the carbon skeleton increases.

(B) Method of Depositing Nitrogen-Containing Carbon on the Surface of Carbonaceous Gel by Thermal CVD This is the method to introduce a nitrogen-containing organic compound to pores of a carbonaceous gel and to allow the nitrogen-containing organic compound to pyrolytically decompose so as to deposit nitrogen-containing carbon on the surface of the carbonaceous gel. In the first step, a carbonaceous gel is set in a reaction tube and heated to a predetermined temperature while introducing inert gas such as nitrogen or argon to the reaction tube. In the next step, while maintaining the heated state, a nitrogen-containing organic compound in a gaseous state is introduced in the reaction tube so as to introduce the nitrogen-containing organic compound to pores of the carbonaceous gel, thus, the CVD reaction is performed for a predetermined period of time. Thereby, a nitrogen-containing carbon with the skeleton structure formed by carbon atom and nitrogen atom can be deposited in pores of the carbonaceous gel. The deposition by the thermal CVD is generally performed under an inert gas atmosphere such as nitrogen or argon, because carbon burns if the reaction is performed under an oxidative atmosphere.

The nitrogen-containing organic compound used herein is not particularly limited if it is an organic compound containing nitrogen atom. Examples thereof are nitrogen-containing heterocyclic compounds, amines, imines and nitrites. Examples of the nitrogen-containing heterocyclic compounds are nitrogen-containing heteromonocyclic compounds and nitrogen-containing condensed heterocyclic compounds.

Examples of the nitrogen-containing monocyclic compounds are five-membered ring compounds including pyrrole and derivatives thereof, and diazoles such as pyrazole, imidazole and derivatives thereof; and six-membered ring compounds including pyridine and derivatives thereof, diazines such as pyridazine, pyrimidine, pyrazine and derivatives thereof, triazines, and triazine derivatives such as melamine and cyanuric acid.

Examples of the nitrogen-containing condensed heterocyclic compounds are quinoline, phenanthroline and purine.

Examples of the amines are primary to tertiary amine, diamines, triamines, polyamines and amino compounds.

Examples of the primary to tertiary amine are aliphatic amine such as methylamine, ethylamine, dimethylamine and trimethylamine, and aromatic amine such as aniline and derivatives thereof.

Examples of the amino compounds are aminoalcohol such as ethanolamine.

Examples of the imines are pyrrolidine and ethylimine.

Examples of the nitriles are aliphatic nitrile such as acetonitrile, and aromatic nitrile such as benzonitrile.

Examples of other nitrogen-containing organic compounds are polyamides such as nylon, amino sugars such as galactosamine, nitrogen-containing polymers such as polyacrylonitrile, amino acid and polyimides.

When the nitrogen-containing organic compound is in a liquid state at ordinary temperatures in the deposition of the thermal CVD, the nitrogen-containing organic compound can be vaporized so as to be in a gaseous state with the use of a bubbler, a mass flow pump or the like, and introduced to the reaction tube. In this case, it is preferable to introduce the nitrogen-containing organic compound in the gaseous state using nitrogen, argon or the like as carrier gas. Further, in order to prevent the gas once flowed through the reaction tube from flowing backward from the outlet side of the reaction tube, it is preferable to prevent backward flow, for example, by providing a bubbler having liquid paraffin or the like on the outlet side of the reaction tube.

If the nitrogen-containing organic compound is in a solid state at ordinary temperatures, a thermal evaporator (sublimator) may be provided on the inlet side of the reaction tube to heat the nitrogen-containing organic compound to be in a gaseous state and to introduce the gas to the reaction tube. The temperature of the evaporator needs to be adjusted so that the nitrogen-containing organic compound does not pyrolytically decompose.

If the nitrogen-containing organic compound is polymerizable, the nitrogen-containing organic compound may be preliminarily polymerized in the pores of the carbonaceous gel, and then, thermally decomposed in the reaction tube under an inert atmosphere.

Further, if the nitrogen-containing organic compound does not vaporize with heating, the nitrogen-containing organic compound may be preliminarily introduced in the pores of the carbonaceous gel by a solution adsorption method, a method of evaporation to dry or the like, and thermally decomposed in an inert atmosphere so as to allow the nitrogen-containing carbon to deposit in the pores of the carbonaceous gel.

The reaction temperature in the deposition of the thermal CVD may not be particularly limited, if it is a temperature at which the nitrogen-containing organic compound pyrolytically decomposes and carbonizes, but may be preferably 300 to 1000° C., more preferably 500 to 700° C. If the reaction temperature is less than 300° C., the nitrogen-containing organic compound is less likely to be pyrolytically decomposed, and the deposition rate of nitrogen-containing carbon lowers so that the reaction time and energy consumption tend to increase. On the other hand, if the reaction temperature exceeds 1,000° C., carbon is less likely to remain in the carbon skeleton so that the N/C ratio decreases.

In the deposition, the deposition amount of the nitrogen-containing carbon deposited in the pore of the carbonaceous gel may not be particularly limited, but may be preferably $(0.0001 \times Y)$ g or more, when a specific surface area per 1 g of carbonaceous gel is Y m$^2$. If the deposition amount of nitrogen-containing carbon is less than $(0.0001 \times Y)$ g, the deposition amount is small so that the improvement in adsorption by nitrogen atom may not be achieved.

There is a correlation between the deposition amount and the CVD reaction time. Thus, by adjusting the CVD reaction time, the deposition amount can be controlled. Further, the deposition amount varies due to CVD reaction temperature, kind of carbonaceous gel, kind of nitrogen-containing organic compound, flow rate of introducing nitrogen-containing organic compound or the like. In all cases, the deposition amount can be adjusted by adjusting the CVD reaction time.

Next, a method of producing the enzymatic electrode of the present invention will be explained.

In the first step, a surface of carbonaceous porous body is subject to support enzyme. A method of supporting enzyme may not be particularly limited. Various methods such as sublimation and impregnation can be used, but the impregnation method is suitable.

Enzyme support by the impregnation method is as follows. In the first step, the enzyme is dissolved in water or a buffer solution at a concentration not to cause precipitation, preferably 0.1 to 1000 mg/ml. In the next step, in the solution, a powdered carrier is suspended or a sheeted carrier is immersed at a temperature not to freeze the solution and not to modify enzyme, preferably 0 to 50° C., to contact the enzyme and the carrier. The contacting time is preferably at least 5 minutes or more, more preferably 30 minutes or more. Thereby, the enzyme is immobilized on the surface of carrier or in the pore.

The concentration of carrier to be suspended in the solution is not particularly limited, but about 0.1 to 1000 mg/ml is preferable. Also, after the supporting step, centrifugation or the like may be further performed to separate the carrier and the solution. Alternatively, the liquid component may be removed by drying or the like.

A method to support a mediator on the carrier may be the same as with the method to support the enzyme on the carrier.

Also, the enzyme and the electron transfer mediator may be supported on the carrier at the same time.

Next, effects of electrocatalyst and enzymatic electrode of the present invention will be explained.

FIG. 1 shows a molecular structure of CueO from *Escherichia coli*, which is a kind of multi-copper oxidase (Sue A. Roberts et al., PNAS, vol. 99 (2002), pp. 2766-2771). As shown in FIG. 1, CueO has mononuclear blue copper (type I Cu) functioning as an electron transfer gate and a trinuclear copper cluster (type II Cu, type III Cu) being an active center in a three-dimensional structure of the protein molecule. The mononuclear blue copper and the trinuclear copper cluster are located inside of different openings (Kunishige Kataoka, BIOCHEMISTRY, vol. 77 (2005), pp. 148-153). Also, one of two openings is located on the front face of three-dimensional structure of the protein molecule, and the other on the rear face thereof. Further, the wild type CueO has the upper part of mononuclear blue copper covered by a helical segment called as Helix 5.

By using CueO as the electrocatalyst for enzymatic electrode, current density higher than that of conventional oxidoreductases can be obtained.

While the reason is not known in detail, it is considered as follows:

(1) since the active center, which catalyzes the oxidation reaction, and the electron transfer gate are separated in the enzyme molecule of CueO, the catalytic reaction and the electron transfer reaction can be simultaneously achieved, even if the enzyme is immobilized on a solid surface of electrode; and (2) since the electron transfer gate of CueO is located closer to the molecular surface than that of the conventional enzymes, the distance between the electron transfer gate and the electrode decreases, when the CueO molecule is immobilized on the solid surface so that efficiency of electron transfer improves.

Also, by using a carbonaceous porous body having predetermined pore size, pore distribution and specific surface area high current density can be obtained, when the CueO is immobilized on the carrier.

The reason is considered to be as follows:

(1) since most of enzyme molecules can be immobilized in the pore of carbonaceous porous body, the electron transfer between the carrier and the enzyme is facilitated; and (2) since a porous wall inhibits a change in the three-dimensional structure of the protein molecule, deactivation by heat is reduced so that thermal stability improves.

Also, if the carbonaceous gel is used as the carbonaceous porous body, high electron transfer efficiency can be obtained. The reason is considered that the carbonaceous gel has a large quantity of pores suitable to support the enzyme and that a three-dimensional network of pores mutually connected is formed and so on.

Further, if the nitrogen-containing carbonaceous gel is used as the carbonaceous porous body, high electron transfer efficiency can be maintained for a long period of time. The reason is considered to be that a polar group is introduced in the inner porous wall by introducing nitrogen to the carbonaceous gel so that a new bond such as a hydrogen bond is generated between the polar group and a hydrophilic group on the surface of the protein molecule.

EXAMPLES

Example 1, Comparative Examples 1 and 2

1. Test Method

CueO from *Escherichia coli* (Example 1), laccase from *Rhus verniciflua verniciflua* (Comparative example 1) and bilirubin oxidase (BOD) derived from *Myrotheciumu* sp. (Comparative example 2) were respectively dissolved in a phosphate buffer solution (0.05 M, pH7.0) to prepare an enzyme solution of 8 µM respectively.

The enzyme solution was saturated with oxygen. Then, the enzyme solution was used to evaluate a direct electron transfer property between the enzyme and the electrode by the cyclic voltammetry (potential: −50 to 650 mV; sweep rate: 20 mV/sec) using an HOPG (highly oriented pyrolytic graphite) electrode as a working electrode. As a counter electrode, a platinum electrode was used. As a reference electrode, a silver/silver chloride electrode was used.

2. Result

Figure 2:
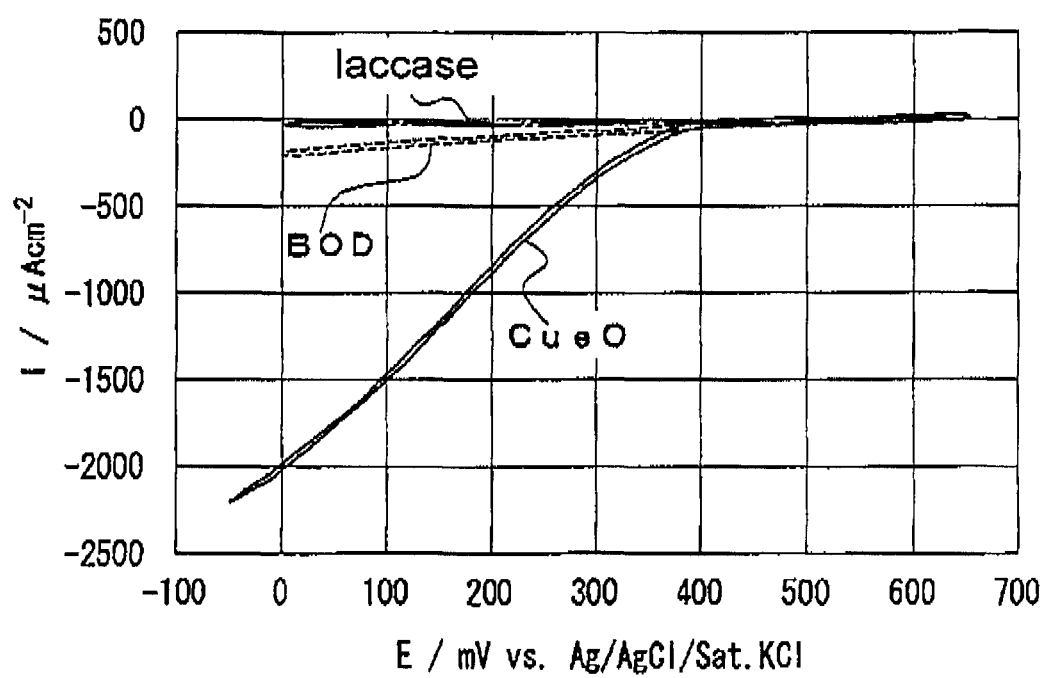
FIG. 2 shows cyclic voltammograms of the enzyme solutions containing various multi-copper oxidases.

FIG. 2 shows a cyclic voltammogram. FIG. 2 shows that each oxidation current density of laccase (Comparative example 1) and SOD (Comparative example 2) in static condition at 0 V is −500 µA/cm² or less, while the oxidation current density of CueO from *Escherichia coli* in static condition at 0 V is about −2000 µA/cm².

Examples 2 and 3, Comparative Examples 3 and 4

1. Preparation of Carbonaceous Gel 5.5 g of resorcinol (manufactured by Wako Pure Chemical Industries, Ltd.) and 26.5 mg of sodium carbonate (manufactured by Wako Pure Chemical Industries, Ltd.) were dissolved in 16.9 g of distilled water. Then, 8.1 g of 37% formaldehyde solution (manufactured by Wako Pure Chemical Industries, Ltd.) was added followed by agitation to mix. The mixed solution became faint yellow and transparent. A molar ratio of added components was resorcinol:sodium carbonate:formaldehyde=200:1:400.

In the next step, water was added to the obtained concentrate solution to dilute as twice as large in volume ratio. The diluted solution was charged in a vial container and sealed to leave for 24 hours at room temperature, 24 hours at 50° C., and further 72 hours at 90° C., thus obtained a hydrated organic gel.

In the next step, in order to remove moisture in the organic gel, the organic gel was immersed in acetone (manufactured by Wako Pure Chemical Industries, Ltd.) to exchange solvent. When the organic gel is immersed in the acetone, the moisture in the organic gel diffuses in the acetone, and the moisture in the gel can be replaced with the acetone. The acetone was repeatedly exchanged with new one for several times, when the diffusion of moisture was saturated in order to substitute the moisture in the gel completely with acetone. In the next step, the immersion solvent was changed to n-pentane (manufactured by Wako Pure Chemical Industries, Ltd.). The exchange of solvent and the immersion were repeated until the acetone in the organic gel was completely replaced with n-pentane. Further, the organic gel was air-dried to obtain a dried organic gel.

The obtained dried organic gel was heated under a nitrogen flow (flow rate: 300 ml/min) at 1000° C. to carbonize the organic gel. The time for heating was 6 hours.

2. Preparation of Enzymatic Electrode

Each of 6.7% of carbonaceous gel (Example 2) and Ketjenblack (Example 3) was suspended in an NMP (N-Methylpyrrolidone) solution containing 5% PDVF (polyvinylidene difluoride) to prepare a slurry. The surface of a glassy carbon electrode (manufactured by BAS Inc.; product number: 002012) having a diameter of 6 mm was coated with the carbon carrier by adding the above slurry followed by performing spincoat (3000 rpm). The obtained carbon modified electrode was immersed in the solution of CueO from *Escherichia coli* (12.5 mg/ml) overnight at 4° C. Thereby, the enzyme was immobilized on the carbon modified electrode.

Also, according to a similar method, laccase from *Rhus verniciflua* was immobilized on each of a carbonaceous gel modified electrode (Comparative example 3) and a Ketjenblack modified electrode (Comparative example 4).

3. Test Method

The electric properties of the electrode were evaluated by the cyclic voltammetry (potential: 200 to 500 mV, sweep rate 20 mV/sec) using each of enzymatic electrodes obtained in the above [2.] as the working electrode. As the counter electrode, a platinum electrode was used. As the reference electrode, a silver-silver chloride electrode was used. As an electrolyte, a 50 mM potassium phosphate buffer solution (pH7.0) saturated with oxygen was used. Further, the evaluation of electric properties was performed at static conditions for both electrolytic solution and enzymatic electrode.

4. Result

Figure 3:
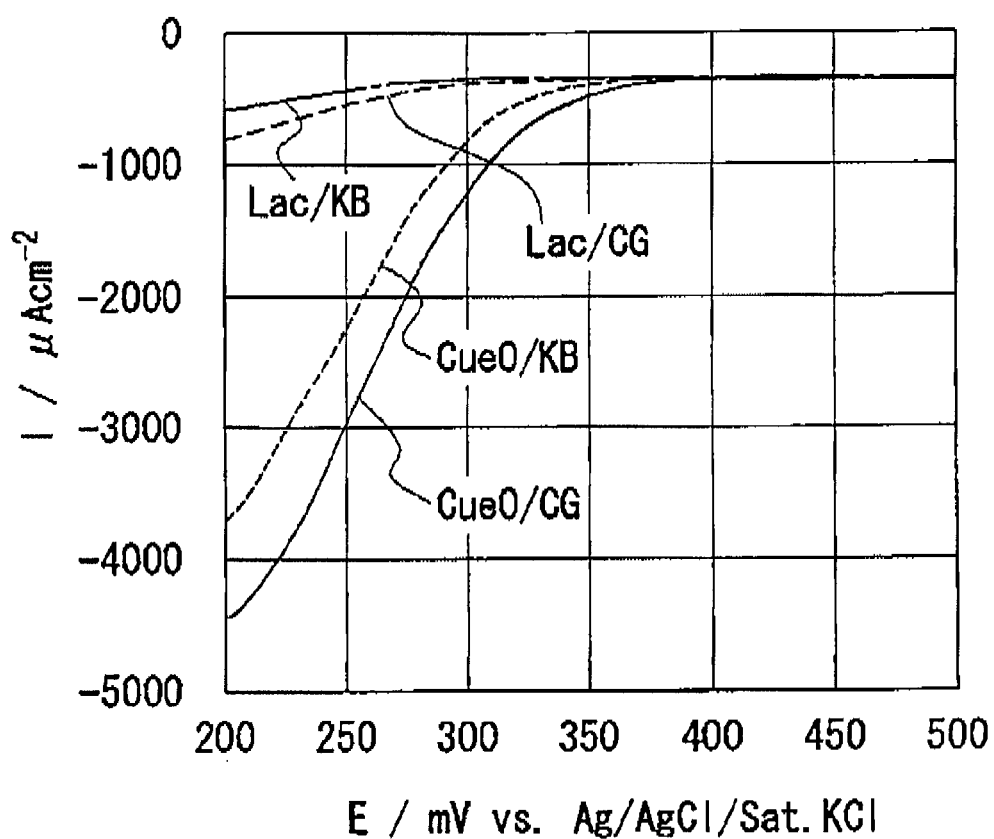
FIG. 3 shows cyclic voltammograms of the enzymatic electrode containing various multi-copper oxidases supported by various carbon carriers.

FIG. 3 is a cyclic voltammogram. FIG. 3 shows that the amount of current increases by using the carbonaceous gels with laccase and CueO, respectively, in comparison to using the Ketjenblack. Particularly, when using CueO and CG in combination, the current density at 200 mV increased by about seven times in comparison with the case using laccase and KB in combination.

The embodiments of the present invention are explained in detail as above. The present invention may not be limited to the above embodiments, and various changes may be made without departing from the scope of the present invention.

INDUSTRIAL APPLICABILITY

The electrocatalyst according to the present invention can be used for electrochemical devices such as biosensors and fuel cells, and solar cells.

Also, the enzymatic electrode of the present invention can be used for electrochemical devices such as biosensors and fuel cells, and solar cells.

The invention claimed is:

1. An electrocatalyst made of CueO from *Escherichia coli*.

2. An enzymatic electrode comprising a carbonaceous porous body and an electrocatalyst made of CueO from *Escherichia coli* supported on a surface of the carbonaceous porous body.

3. The enzymatic electrode according to claim 2, wherein the carbonaceous porous body is carbonaceous gel which satisfies the following conditions (I) and (II):
   (I) there is no X-ray diffraction peak in the scan region $2\theta=0.5°$ to $10°$ (CuKα); and
   (II) in a pore size distribution calculated from an adsorption-desorption isotherm,
   in the case that a pore size of distribution peak top is in the range from 2 nm or more to less than 10 nm (pore size "d"), 60% or more of total pore volume is in the pore size range of d±2 nm, and
   in the case that the pore size of the distribution peak top is in the range from 10 nm or more to 50 nm or less (pore size "D"), 60% or more of total pore volume is in the pore size range of from (0.75×D) nm to (1.25×D) nm.

4. The enzymatic electrode according to claim 2, wherein the enzymatic electrode does not contain a mediator which facilitates transfer of electron between the carbonaceous porous body and said CueO.

5. A method of generating power comprising supplying oxygen to an electrode for oxygen reduction using CueO from *Escherichia coli* as an electrocatalyst.

6. A battery comprising an electrode for oxygen reduction using CueO from *Escherichia coli* as an electrocatalyst at a cathode.

7. A biosensor comprising an electrode for oxygen reduction using CueO from *Escherichia coli* as an electrocatalyst.

8. The enzymatic electrode according to claim 3, wherein the enzymatic electrode does not contain a mediator which facilitates transfer of electron between the carbonaceous porous body and said CueO.

* * * * *

SEQUENCE LISTING

```
<160> NUMBER OF SEQ ID NOS: 1

<210> SEQ ID NO 1
<211> LENGTH: 488
<212> TYPE: PRT
<213> ORGANISM: Escherichia coli
```

```
<400> SEQUENCE: 1

Ala Glu Arg Pro Thr Leu Pro Ile Pro Asp Leu Leu Thr Thr Asp Ala
1               5                   10                  15

Arg Asn Arg Ile Gln Leu Thr Ile Gly Ala Gly Gln Ser Thr Phe Gly
            20                  25                  30

Gly Lys Thr Ala Thr Thr Trp Gly Tyr Asn Gly Asn Leu Leu Gly Pro
        35                  40                  45

Ala Val Lys Leu Gln Arg Gly Lys Ala Val Thr Val Asp Ile Tyr Asn
    50                  55                  60

Gln Leu Thr Glu Glu Thr Thr Leu His Trp His Gly Leu Glu Val Pro
65                  70                  75                  80

Gly Glu Val Asp Gly Pro Gln Gly Ile Ile Pro Pro Gly Gly Lys
                85                  90                  95

Arg Ser Val Thr Leu Asn Val Asp Gln Pro Ala Ala Thr Cys Trp Phe
            100                 105                 110

His Pro His Gln His Gly Lys Thr Gly Arg Gln Val Ala Met Gly Leu
        115                 120                 125

Ala Gly Leu Val Val Ile Glu Asp Asp Glu Ile Leu Lys Leu Met Leu
    130                 135                 140

Pro Lys Gln Trp Gly Ile Asp Asp Val Pro Val Ile Val Gln Asp Lys
145                 150                 155                 160

Lys Phe Ser Ala Asp Gly Gln Ile Asp Tyr Gln Leu Asp Val Met Thr
            165                 170                 175

Ala Ala Val Gly Trp Phe Gly Asp Thr Leu Leu Thr Asn Gly Ala Ile
        180                 185                 190

Tyr Pro Gln His Ala Ala Pro Arg Gly Trp Leu Arg Leu Arg Leu Leu
    195                 200                 205

Asn Gly Cys Asn Ala Arg Ser Leu Asn Phe Ala Thr Ser Asp Asn Arg
210                 215                 220

Pro Leu Tyr Val Ile Ala Ser Asp Gly Gly Leu Leu Pro Glu Pro Val
225                 230                 235                 240

Lys Val Ser Glu Leu Pro Val Leu Met Gly Glu Arg Phe Glu Val Leu
            245                 250                 255

Val Glu Val Asn Asp Asn Lys Pro Phe Asp Leu Val Thr Leu Pro Val
        260                 265                 270

Ser Gln Met Gly Met Ala Ile Ala Pro Phe Asp Lys Pro His Pro Val
    275                 280                 285

Met Arg Ile Gln Pro Ile Ala Ile Ser Ala Ser Gly Ala Leu Pro Asp
        290                 295                 300

Thr Leu Ser Ser Leu Pro Ala Leu Pro Ser Leu Glu Gly Leu Thr Val
305                 310                 315                 320

Arg Lys Leu Gln Leu Ser Met Asp Pro Met Leu Asp Met Met Gly Met
            325                 330                 335

Gln Met Leu Met Glu Lys Tyr Gly Asp Gln Ala Met Ala Gly Met Asp
        340                 345                 350

His Ser Gln Met Met Gly His Met Gly His Gly Asn Met Asn His Met
    355                 360                 365

Asn His Gly Gly Lys Phe Asp Phe His His Ala Asn Lys Ile Asn Gly
    370                 375                 380

Gln Ala Phe Asp Met Asn Lys Pro Met Phe Ala Ala Ala Lys Gly Gln
385                 390                 395                 400

Tyr Glu Arg Trp Val Ile Ser Gly Val Gly Asp Met Met Leu His Pro
            405                 410                 415
```

-continued

```
Phe His Ile His Gly Thr Gln Phe Arg Ile Leu Ser Glu Asn Gly Lys
        420                 425                 430

Pro Pro Ala Ala His Arg Ala Gly Trp Lys Asp Thr Val Lys Val Glu
        435                 440                 445

Gly Asn Val Ser Glu Val Leu Val Lys Phe Asn His Asp Ala Pro Lys
        450                 455                 460

Glu His Ala Tyr Met Ala His Cys His Leu Leu Glu His Glu Asp Thr
465                 470                 475                 480

Gly Met Met Leu Gly Phe Thr Val
                485
```